United States Patent [19]

Collins et al.

[11] Patent Number: 5,686,480
[45] Date of Patent: Nov. 11, 1997

[54] FUSED TRICYCLIC HETEROAROMATIC DERIVATIVES AS DOPAMINE RECEPTOR SUBTYPE LIGANDS

[75] Inventors: Ian James Collins, Ware; Paul David Leeson, Cambridge; Michael Rowley, Harlow, all of United Kingdom

[73] Assignee: Merck, Sharp & Dohme, Ltd., Hoddesdon, England

[21] Appl. No.: 605,096

[22] PCT Filed: Sep. 6, 1994

[86] PCT No.: PCT/GB94/01935

§ 371 Date: Mar. 1, 1996

§ 102(e) Date: Mar. 1, 1996

[87] PCT Pub. No.: WO95/07262

PCT Pub. Date: Mar. 16, 1995

[30] Foreign Application Priority Data

Sep. 9, 1993 [GB] United Kingdom ............... 9318691

[51] Int. Cl.6 .................................................. A61K 43/56
[52] U.S. Cl. ........................... 514/403; 544/371; 546/176; 546/199; 548/359.1; 548/359.5
[58] Field of Search .................... 548/359.1, 359.5; 514/403; 544/371; 546/199, 176

[56] References Cited

U.S. PATENT DOCUMENTS 3,553,230 1/1971 Freedman .
3,969,527 7/1976 Krapcho et al. ........................ 424/273

FOREIGN PATENT DOCUMENTS 0 402 644 5/1990 European Pat. Off. .
0402644 12/1990 European Pat. Off. .
9410162 5/1994 WIPO .
WO94/10162 11/1994 WIPO .

OTHER PUBLICATIONS

J. of Med. Chem., 27, 12, 1984, pp. 1607–1613, J. M. Jones et al.

J. H. Jones et al. 'Synthesis of 4–Substituted 2H–naphth[1, 2–b]–1,4–oxazines, A New Class of Dopamine Agonists' Journal of Medicinal Chemistry, vol. 27, No. 12, 1984 pp. 1607–1613.

G. Haeusler et al. 'Pharmacological Basis For Hypertensive Therapy With A Novel Dopamine Agonist' Chemical Abstracts vol. 118, No. 9, Mar. 1, 1993 No 72912b.

*Primary Examiner*—Mukund J. Shah
*Assistant Examiner*—Michael Bucknum
*Attorney, Agent, or Firm*—Robert J. North; Melvin Winokur

[57] ABSTRACT

A class of fused tricyclic heteroaromatic compounds of formula (I), or a salt thereof or a prodrug thereof containing a fused pyrazole ring are ligands for dopamine receptor subtypes within the body and are therefore of use in the treatment and/or prevention of disorders of the dopamine system, such as schizophrenia.

6 Claims, No Drawings

FUSED TRICYCLIC HETEROAROMATIC DERIVATIVES AS DOPAMINE RECEPTOR SUBTYPE LIGANDS

This application is a 371 of PCT/GB94/01935 filed Sep. 6, 1994.

This invention relates to a particular class of fused tricyclic heteroaromatic compounds based on a substituted pyrazole moiety. These compounds are ligands for dopamine receptor subtypes within the body and are therefore of use in the treatment and/or prevention of disorders of the dopamine system, including schizophrenia, depression, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London), 1991, 350, 610) and $D_5$ (Sunahara et al., Nature (London), 1991, 350, 614) receptor subtypes have been described.

In DE-A-2119977 there is described and claimed inter alia a class of 3-(substituted-amino)methylnaphth[1,2-c]isoxazoles, and processes for their preparation. No utility is, however, ascribed in DE-A-2119977 to the compounds described therein.

U.S. Pat. Nos. 3,553,230 and 3,825,539 describe a range of 4H[1]benzopyrano[3,4-d]isoxazole derivatives. The compounds of U.S. Pat. No. 3,553,230 are stated to have utility as muscle relaxants and antidepressant agents, whilst those of U.S. Pat. No. 3,825,539 are stated to possess central nervous system depressant and anti-inflammatory activity. In addition, the compounds of both publications are alleged to be useful as intermediates in the preparation of pickling inhibitors, wood preservatives and moth proofing agents. In neither publication, however, is there any suggestion that the compounds described therein would be of any assistance in treating disorders of the dopamine system.

The compounds in accordance with the present invention, being ligands for dopamine receptor subtypes within the body, are accordingly of use in the treatment and/or prevention of disorders of the dopamine system.

The present invention accordingly provides a compound of formula I, or a salt thereof or a prodrug thereof:

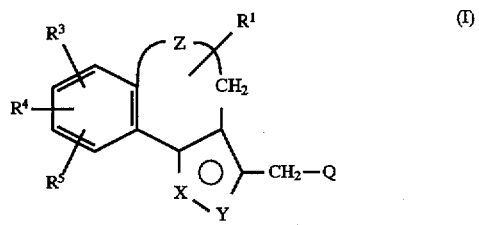

wherein the broken circle represents two non-adjacent double bonds whereby the five-membered ring containing X and Y is aromatic;

one of X and Y represents nitrogen, and the other of X and Y represents $N-R^2$;

Z represents a chemical bond, an oxygen or sulphur atom, or a methylene group;

Q represents a substituted, or aryl-fused, five- or six-membered monocyclic heteroaliphatic ring containing one or two nitrogen atoms and optionally one oxygen atom;

$R^1$ and $R^2$ independently represent hydrogen or $C_{1-6}$ alkyl;

$R^3$, $R^4$ and $R^5$ independently represent hydrogen, hydrocarbon, a heterocyclic group, halogen, cyano, trifluoromethyl, nitro, $-OR^a$, $-SR^a$, $-SOR^a$, $SO_2R^a$, $-SO_2NR^aR^b$, $-NR^aR^b$, $-NR^aCOR^b$, $-NR^aCO_2R^b$, $-COR^a$, $-CO_2R^a$ or $-CO_2NR^aR^b$; and $R^a$ and $R^b$ independently represent hydrogen, hydrocarbon or a heterocyclic group.

As will be appreciated, the five-membered heteroaromatic ring containing the moieties X and Y in formula I above is a substituted pyrazole ring.

The monocyclic heteroaliphatic ring Q in the compounds of formula I above is suitably a substituted pyrrolidinyl, piperidinyl, tetrahydropyridinyl, morpholinyl or piperazinyl ring, or an optionally substituted dihydroisoindolyl or tetrahydroisoquinolinyl ring, preferably linked through a nitrogen atom. Examples of suitable rings for the substituent Q include the moieties of formula Qa, Qb, Qc and Qd:

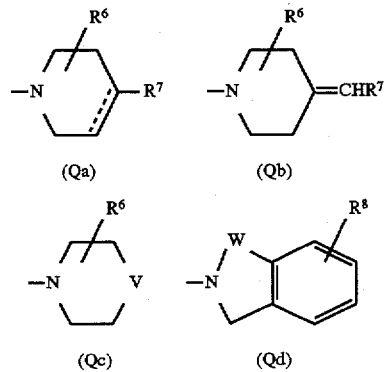

in which the broken line represents an optional chemical bond;

V represents an oxygen atom or a moiety of formula $N-R^7$;

$R^6$ represents hydrogen, or an optionally substituted $C_{1-6}$ alkyl, $C_{1-6}$ alkoxy, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$) alkyl, aryl($C_{1-6}$)alkoxy, aryl($C_{2-6}$)alkenyl, aryl($C_{2-6}$) alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl ($C_{2-6}$)alkynyl group;

$R^7$ represents an optionally substituted $C_{1-6}$ alkyl, $C_{1-6}$ alkoxy, $C_{2-6}$ alkenyl, $C_{2-6}$ alkynyl, $C_{3-7}$ cycloalkyl, $C_{3-7}$ cycloalkyl( $C_{1-6}$)alkyl, aryl, aryl($C_{1-6}$)alkyl, aryl($C_{1-6}$) alkoxy, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$) alkyl, heteroaryl($C_{2-6}$)alkenyl or heteroaryl($C_{2-6}$)alkynyl group;

W represents —$CH_2$— or —$CH_2CH_2$—; and $R^8$ represents hydrogen, $C_{1-6}$ alkyl, $C_{1-6}$ alkoxy, aryl, aryl($C_{1-6}$)alkyl or halogen.

The compounds of the present invention are preferably prepared and utilised in the form of a free base or as a pharmceutically acceptable salt thereof.

For use in medicine, the salts of the compounds of formula I will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of use in the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$) alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents $R^6$, $R^7$ and $R^8$ include straight-chained and branched alkyl groups containing from 1 to 6 carbon atoms. Typical examples include methyl and ethyl groups, and straight-chained or branched propyl and butyl groups. Particular alkyl groups are methyl, ethyl, isopropyl and t-butyl.

Suitable alkenyl groups within the scope of the term "hydrocarbon" and within the definition of the substituents $R^6$ and $R^7$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^6$ and $R^7$ include straight-chained and branched alkynyl groups containing from 2 to 6 carbon atoms. Typical examples include ethynyl and propargyl groups.

Suitable cycloalkyl groups within the scope of the term "hydrocarbon" and within the definition of the substituents $R^6$ and $R^7$ include groups containing from 3 to 7 carbon atoms. Particular cycloalkyl groups are cyclopropyl and cyclohexyl.

A particular $C_{3-7}$ cycloalkyl($C_{1-6}$)alkyl group within the scope of the term "hydrocarbon" and within the definition of the substituents $R^6$ and $R^7$ is cyclohexylethyl.

Particular aryl groups within the scope of the term "hydrocarbon" and within the definition of the substituents $R^6$, $R^7$ and $R^8$ include phenyl and naphthyl.

Particular aryl($C_{1-6}$)alkyl groups within the scope of the term "hydrocarbon" and within the definition of the substituents $R^6$, $R^7$ and $R^8$ include benzyl, naphthylmethyl, phenethyl and phenylpropyl.

A particular aryl($C_{2-6}$)alkenyl group within the scope of the term "hydrocarbon" and within the definition of the substituents $R^6$ and $R^7$ is phenylethenyl.

A particular aryl($C_{2-6}$)alkynyl group within the scope of the term "hydrocarbon" and within the definition of the substituents $R^6$ and $R^7$ is phenylethynyl.

Suitable heterocycloalkyl groups include azetidinyl, pyrrolidyl, piperidyl, piperazinyl, morpholinyl and tetrahydrofuryl groups.

A particular $C_{3-7}$ heterocycloalkyl($C_{1-6}$)alkyl group within the scope of the expression "a heterocyclic group" and within the definition of the substituents $R^6$ and $R^7$ is tetrahydrofurylethyl.

Suitable heteroaryl groups within the scope of the expression "a heterocyclic group" and within the definition of the substituents $R^6$ and $R^7$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, imidazolyl, oxadiazolyl and thiadiazolyl groups.

Particular heteroaryl($C_{1-6}$)alkyl groups within the scope of the expression "a heterocyclic group" and within the definition of the substituents $R^6$ and $R^7$ include thienylmethyl, pyridylmethyl, pyrimidinylmethyl, pyrazinylmethyl and furylethyl.

A particular heteroaryl($C_{2-6}$)alkenyl group within the scope of the expression "a heterocyclic group" and within the definition of the substituents $R^6$ and $R^7$ is thienylethenyl.

The hydrocarbon and heterocyclic groups, as well as the substituents $R^6$ and $R^7$, may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoromethanesulphonyloxy, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$PO(OR^v)$ $(OR^w)$, —$CONR^vR^w$, —$SO_2NR^vR^w$ and —$CH_2SO_2NR^vR^w$, in which $R^v$ and $R^w$ independently represent hydrogen, $C_{1-6}$ alkyl, aryl or aryl ($C_{1-6}$)alkyl.

The term "halogen" as used herein includes fluorine, chlorine, bromine and iodine, especially chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

Suitably, the substituents $R^1$ and $R^2$ independently represent hydrogen or methyl, especially hydrogen.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, methyl, methoxy and benzyloxy.

Suitably, the substituent $R^6$ represents hydrogen.

Suitable values for the substituent $R^7$ include $C_{1-6}$ alkyl, aryl, aryl($C_{1-6}$)alkyl, aryl($C_{2-6}$)alkenyl, aryl($C_{2-6}$)alkynyl, heteroaryl, heteroaryl($C_{1-6}$)alkyl, heteroaryl($C_{2-6}$)alkenyl and heteroaryl($C_{2-6}$)alkynyl, any of which groups may be optionally substituted. Examples of optional substituents on the group $R^7$ include $C_{1-6}$ alkyl, halogen, trifluoromethyl, $C_{1-6}$ alkoxy, nitro, $C_{1-6}$ alkylamino and di($C_{1-6}$)alkylamino.

Particular values of $R^7$ include methyl, ethyl, n-propyl, isopropyl, phenyl, methylphenyl, ethylphenyl, chlorophenyl, dichlorophenyl, iodophenyl, trifluoromethyl-phenyl, methoxyphenyl, ethoxyphenyl, nitrophenyl, dimethylamino-phenyl, benzyl, chlorobenzyl, phenethyl, phenyl-ethenyl, phenyl-ethynyl, chloropyridyl, quinolyl, isoquinolyl, indolyl, furylethyl and furylethenyl.

Particular values of $R^8$ include hydrogen, phenyl, chloro and bromo.

A particular sub-class of compounds in accordance with the invention is represented by the compounds of formula IIA, and salts and prodrugs thereof:

(IIA)

wherein

Z is as defined with reference to formula I above;

—T—U represents —CH$_2$N—, —CH$_2$CH— or —CH=C—;

A represents —(CH$_2$)$_n$— or —CH=CH—;

n is zero, 1, 2 or 3;

B represents a group of formula (i), (ii), (iii) or (iv):

(i) (ii) (iii) (iv)

in which E represents oxygen, sulphur or NH; and $R^{13}$ and $R^{19}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkoxycarbonyl.

Particular values of $R^{13}$ include hydrogen, fluoro, chloro, methyl, ethyl, methoxy and benzyloxy.

Particular values of $R^{19}$ include hydrogen, methyl, ethyl, chloro, iodo, trifluoromethyl, methoxy, ethoxy, nitro and dimethylamino.

Another sub-class of compounds according to the invention is represented by the compounds of formula IIB, and salts and prodrugs thereof:

(IIB)

wherein

Z is as defined with reference to formula I above;

W represents —CH$_2$— or —CH$_2$CH$_2$—;

$R^{13}$ is as defined with reference to formula IIA above; and $R^{18}$ represents hydrogen, $C_{1-6}$ alkyl, $C_{1-6}$ alkoxy, aryl, aryl($C_{1-6}$)alkyl or halogen.

Particular values of $R^{18}$ include hydrogen, phenyl, chloro and bromo, especially hydrogen.

Specific compounds within the scope of the present invention include:

3-[4-(4-methoxyphenyl)piperazin-1-ylmethyl]-4,5-dihydro-1H-benzo[g]indazole;

3-[4-(5-chloropyridin-2-yl)piperazin-1-ylmethyl]-4,5-dihydro-1H-benzo[g]indazole;

3-(1,2,3,4-tetrahydroisoquinolin-2-ylmethyl)-4,5-dihydro-1H-benzo[g]indazole;

3-[4-(isoquinolin-3-yl)piperazin-1-ylmethyl]-4,5-dihydro-1H-benzo[g]indazole;

3-(4-phenyl-1,2,3,6-tetrahydropyridin-1-ylmethyl)-4,5-dihydro-1H-benzo[g]indazole;

3-[4-(2-(furan-2-yl)ethyl)-1,2,3,6-tetrahydropyridin-1-ylmethyl]-4,5-dihydro-1H-benzo[g]indazole; 3-[4-(2-phenylethyl)-1,2,3,6-tetrahydropyridin-1-ylmethyl]-4,5-dihydro-1H-benzo[g]indazole;

3-(4-phenylpiperidin-1-ylmethyl)-4,5-dihydro-1H-benzo[g]indazole;

3-(4-benzylpiperazin-1-ylmethyl)-4,5-dihydro-1H-benzo[g]
indazole;

3-[4-(quinolin-2-yl)piperazin-1-ylmethyl]-4,5-dihydro-1H-
benzo[g]indazole;

3-[4-((E)-2-phenylethenyl)-1,2,3,6-tetrahydropyridin-1-
ylmethyl]-4,5-dihydro-1H-benzo[g]indazole;

3-[4-(4-methoxyphenyl)piperazin-1-ylmethyl]-1,4-
dihydroindeno[1,2-c]pyrazole;

3-[4-(4-methoxyphenyl)piperazin-1-ylmethyl]benzo[b]-2H-
pyrano[4,3-c]-1H-pyrazole;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of disorders of the dopamine system, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

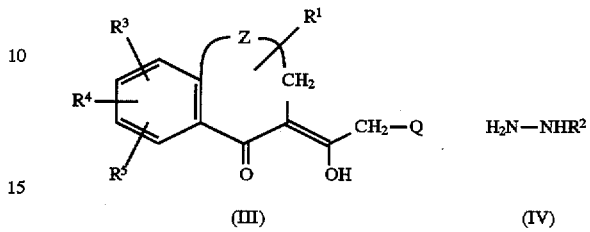

wherein Z, Q, $R^1$, $R^2$, $R^3$, $R^4$ and $R^5$ are as defined above; followed, if necessary, by separation of the resulting mixture of isomers by conventional means.

The reaction is conveniently carried out by stirring the reactants in a suitable solvent, for example a mixture of N,N-dimethylformamide and methanol, optionally in the presence of a non-nucleophilic base such as triethylamine or ethyldiisopropylamine, suitably at room temperature.

As indicated above, the overall reaction between compounds III and IV will usually give rise to a mixture of isomeric products of formula I, in one of which X represents nitrogen and Y represents N—$R^2$, and in the other of which the X and Y moieties are reversed. For this reason, it will generally be necessary to separate the mixture of isomers obtained therefrom by conventional methods such as chromatography.

The compounds of formula III above may be prepared by reacting a carboxylic acid of formula V, or an activated derivative thereof, with two equivalents of a metal enolate of formula VI:

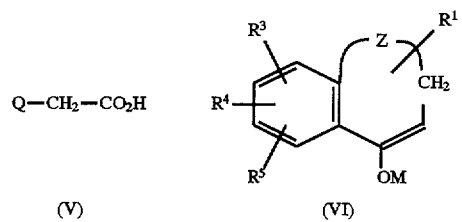

wherein Z, Q, $R^1$, $R^3$, $R^4$ and $R^5$ are as defined above, and M represents a metal capable of providing a suitable counterion for the enolate anion.

The metal M is suitably an alkali metal, especially lithium.

The activated derivative of the carboxylic acid V is suitably the compound formed by reaction between the carboxylic acid V and 1,1'-carbonyldiimidazole, conveniently in tetrahydrofuran at room temperature.

The reaction between compound V, or the activated derivative thereof, and compound VI is suitably carried out in a solvent such as tetrahydrofuran, commencing at −78° C. with warming to 0° C.

The metal enolate of formula VI is ideally prepared by reacting the corresponding carbonyl compound of formula VII:

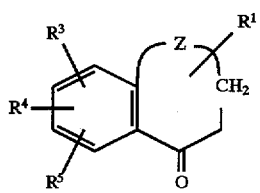

(VII)

wherein Z, $R^1$, $R^3$, $R^4$ and $R^5$ are as defined above; with a non-nucleophilic base such as lithium diisopropylamide, suitably in tetrahydrofuran at −78° C.

In an alternative procedure, the compounds according to the present invention may be prepared by a process which comprises reacting a compound of formula VIII with a compound of formula IX:

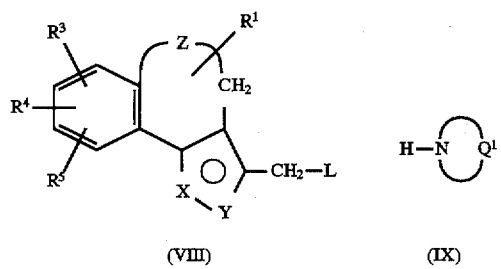

(VIII)   (IX)

wherein X, Y, Z, $R^1$, $R^3$, $R^4$ and $R^5$ are as defined above, $Q^1$ represents the residue of the moiety Q as defined above, and L represents a suitable leaving group.

The leaving group L is suitably a halogen atom, e.g. chlorine or bromine; or a quaternary ammonium cation, e.g. trimethylammonium.

When L represents a halogen atom, the reaction between compounds VIII and IX is conveniently carried out by stirring the reactants under basic conditions in a suitable solvent, for example potassium carbonate in N,N-dimethylformamide, or triethylamine in tetrahydrofuran or acetonitrile. Where L represents a quaternary ammonium cation, the reaction will typically be carried out in the presence of a base such as ethyldiisopropylamine, suitably in N,N-dimethylformamide at an elevated temperature, e.g. approximately 60°–100° C.; or the reagent of formula IX will firstly be lithiated, and then reacted with compound VIII in tetrahydrofuran at room temperature, with subsequent heating to reflux.

Where the leaving group L is, for example, trimethylammonium, the intermediate of formula VIII may suitably be prepared from the corresponding precursor compound of formula X:

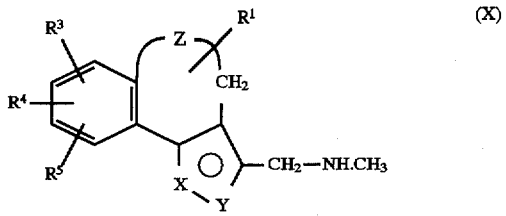

(X)

wherein X, Y, Z, $R^1$, $R^3$, $R^4$ and $R^5$ are as defined above; by sequential methylation reactions using procedures well known from the art. One such procedure comprises reductive methylation using formaldehyde in the presence of sodium cyanoborohydride; followed by a standard methylation reaction using methyl iodide.

The intermediates of formula X may conveniently be prepared by reacting the appropriate compound of formula VI as defined above with the compound of formula BOC—NMe—$CH_2$—$CO_2H$, or an activated derivative thereof, in which BOC denotes the t-butoxycarbonyl protecting group, under conditions analogous to those described above for the reaction between compounds V and VI. The resulting compound is then treated with the reagent of formula IV as defined above, under conditions analogous to those described above for the reaction between compounds III and IV, and the BOC protecting group is removed at an appropriate stage, to afford the desired intermediate of formula X.

Where the leaving group L is a halogen atom, the intermediate of formula VIII may suitably be prepared from the corresponding compound of formula VIII wherein L is hydroxy. For example, the intermediate VIII where L is chloro may conveniently be prepared from the corresponding hydroxy derivative by treatment with oxalyl chloride in the presence of N,N-dimethylformamide.

The precursor of formula VIII wherein L is hydroxy may in turn conveniently be prepared by reduction of the ester derivative of formula XI:

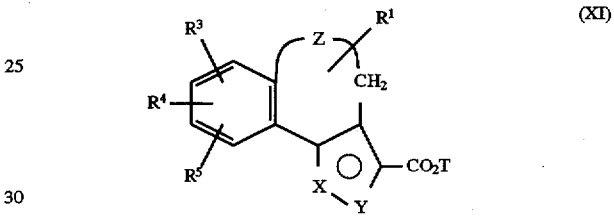

(XI)

wherein X, Y, Z, $R^1$, $R^3$, $R^4$ and $R^5$ are as defined above; and T represents a $C_{1-4}$ alkyl group, typically methyl or ethyl. A suitable reducing agent for effecting this transformation is lithium aluminium hydride.

The intermediates of formula XI may conveniently be prepared by reacting the appropriate compound of formula VI as defined above with an oxalate derivative of formula $(CO_2T)_2$, under conditions analogous to those described above for the reaction between compounds V and VI. The resulting compound is then treated with the reagent of formula IV as defined above, under conditions analogous to those described above for the reaction between compounds III and IV, to afford the desired intermediate of formula XI.

Where they are not commercially available, the starting materials of formula IV, V, VII and IX may be prepared by methods analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein $R^2$ is hydrogen initially obtained may be converted into a corresponding compound wherein $R^2$ represents $C_{1-6}$ alkyl by standard alkylation techniques, such as treatment with an alkyl halide, e.g. methyl iodide, typically under basic conditions, e.g. sodium hydride in N,N-dimethylformamide, or triethylamine in acetonitrile.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–300 µg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 µM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 µM.

EXAMPLE 1

3-(4-(4-Methoxyphenyl)-piperazin-1-ylmethyl)-4,5-dihydro-1H-benzo[g]indazole

A solution of lithium diisopropylamide in THF (300 cm$^3$) was prepared at 0° C. by the addition of n-butyllithium (2.5 mol dm$^{-3}$; 43 cm$^3$) to diisopropylamine (14.9 cm$^3$) under argon. The yellow solution was cooled to −78° C. and α-tetralone (14.1 cm$^3$) in THF (20 cm$^3$) was added dropwise, then stirred for 30 minutes.

Carbonyldiimidazole (8.6 g) was added to a solution of N-tert-butyloxycarbonyl sarcosine (10.0 g) in THF (100 cm$^3$) at 0° C. under argon. After stirring for 15 minutes, the yellow solution was cannulated into the above enolate solution. The mixture was stirred at −78° C. for 30 minutes, then warmed to room temperature. After a further 30 minutes, the thick brown gel was poured into saturated aqueous ammonium chloride (400 cm$^3$). The two phases were separated and the aqueous layer was further extracted with ethyl acetate (200 cm$^3$). The combined organic extracts were dried ($MgSO_4$), filtered and concentrated. Dry flash column chromatography on silica gel, eluting with 10% →30% ethyl acetate-hexane, gave 2-(1-hydroxy-2-(N-tert-butyloxycarbonyl-N-methyl)amino-ethylidene )-3,4-dihydronapthalen-1-one as a claret-coloured oil (10.3 g; 61%); $\delta_H$(360 MHz; d$_6$-DMSO) Mixture of carbamate rotamers and two enol forms of diketone observed; 1.38 and 1.43 (9H, 2 x broad s, NC(O)O$^t$Bu), 2.56–2.62 (2H, m, —CH$_2$—), 2.80–2.92 (5H, m, —CH$_2$— and NCH$_3$), 4.30–4.40 (2H, m, —CH$_2$N), 7.26–7.40 (2H, m, 2 of ArH), 7.47 and 7.61 (1H, 2 x t, J 6, 1 of ArH), 7.78–7.90 (1H, m, 1 of ArH), 15.50 and 15.70 (1H, 2 x broad s, enol-OH ); m/z (CI$^-$; NH$_3$) 317 (M$^-$; 100%).

A solution of 2-(1-hydroxy-2-(N-tert-butyloxycarbonyl-N-methyl)amino-ethylidene)-3,4-dihydronapthalen-1-one (6.0 g) and hydrazine monohydrate (5 cm$^3$) in methanol (50 cm$^3$) was stirred at room temperature under argon for 15 minutes. Methanol was removed by evaporation and the orange residual oil was partitioned between water (100 cm$^3$) and 10% methanol-dichloromethane (2×200 cm$^3$). The organic extracts were dried ($MgSO_4$), filtered and concentrated to give (4,5-dihydro-1H-benzo[g]indazol-3-ylmethyl) -(N-tert-butyloxycarbonyl)-methylamine as an orange foam (5.25 g; 89%); $\delta_H$(360 MHz; d$_6$-DMSO) A 1:1 mixture of two pyrazole tautomers was observed. 1.42 (9H, s, NC(O) O$^t$Bu), 2.58–2.68 (2H, m, —CH$_2$—), 2.74 (3H, broad s, NCH$_3$), 2.86–2.96 (2H, m, —CH$_2$—), 4.38 (2H, broad s, —CH$_2$N), 7.16–7.28 (3H, m, 3 of ArH), 7.56–7.70 (1H, m, 1 of ArH), 12.58 and 13.04 (1H, 2 x broad s, NH); m/z (CI$^+$; NH$_3$) 626 (M$_2$H$^+$; 30%) and 314 (MH$^+$; 100).

A saturated solution of hydrogen chloride gas in ethyl acetate (100 cm$^3$) was added at room temperature to a solution of (4,5-dihydro-1H-benzo[g]indazol-3-ylmethyl)-(N-tert-butyloxycarbonyl)-methylamine (5.1 g) in ethyl acetate (50 cm$^3$). After 5 minutes, crystals of the deprotected amine hydrochloride had begun to form. The mixture was chilled (0° C.) for 90 minutes, then filtered to collect the salt. The salt was partitioned between aqueous sodium carbonate (2 mol dm$^{-3}$; 200 cm$^3$) and ethyl acetate (2×100 cm$^3$). The combined organic extracts were dried ($MgSO_4$), filtered and concentrated to give (4,5-dihydro-1H-benzo[g]indazol-3-ylmethyl)-methylamine as a yellow crystalline solid (3.36 g; 97%); $\delta_H$(360 MHz; d$_6$-DMSO) 2.27 (3H, s, NCH$_3$), 2.66 (2H, t, J 7.7, —CH$_2$—), 2.85 (2H, t, J 7.7, —CH$_2$—), 3.33 (1H, broad s, NH), 3.63 (2H, s, —CH$_2$N), 7.14–7.26 (3H, m, 3 of ArH), 7.63 (1H, d, J 7.0, 1 of ArH) and 12.42 (1H, broad s, NH); m/z (CI$^{30}$ ; NH$_3$) 427 (M$_2$H$^+$; 11%) and 214 (MH$^+$; 100).

A solution of (4,5-dihydro-1H-benzo[g]indazol-3-ylmethyl)-methylamine (3.1 g), sodium cyanoborohydride (1.1 g) and glacial acetic acid (2 cm$^3$) in methanol (50 cm$^3$) was cooled to 0° C. and formaldehyde solution (38% formaldehyde in methanol; 2 cm$^3$) was added. The mixture was stirred at 0° C. for 90 minutes, with mild effervescence observed. The mixture was basified with aqueous sodium hydroxide (1 mol dm$^{-3}$; 30 cm$^3$), diluted with water (50 cm$^3$) and saturated with sodium chloride before extraction with ethyl acetate (2×50 cm$^3$). The organic phases were dried ($MgSO_4$), filtered and concentrated to give (4,5-dihydro-1H-benzo[g]indazol-3-ylmethyl)-dimethylamine as an orange foam (3.17 g; 96%); $\delta_H$(360 MHz; CDCl$_3$) 2.35 [6H, s, N(CH$_3$)$_2$], 2.73 (2H, t, J 7.7, —CH$_2$—), 2.95 (2H, t, J 7.7, —CH$_2$—), 3.59 (2H, s, —CH$_2$N), 7.17–7.26 (3H, m, 3 of ArH) and 7.77 (1H, d, J 7, 1 of ArH); m/z (CI$^+$; NH$_3$) 455 (M$_2$H$^+$; 3%) and 228 (MH$^+$; 100).

A solution of (4,5-dihydro-1H-benzo[g]indazol-3-ylmethyl)-dimethylamine (3.17 g) and methyl iodide (1.5 cm$^3$) in 3:1 diethyl ether-ethanol (40 cm$^3$) was stirred at room temperature under argon for 24 hours. The solvent was removed by evaporation to give a yellow residue, which was washed with diethyl ether to give (4,5-dihydro-1H-benzo[g]indazol-3-ylmethyl)-trimethylammonim iodide as a cream-coloured solid (4.49 g; 88%); δ$_H$(360 MHz; d$_6$-DMSO) 2.77 (2H, t, J 7.8, —CH$_2$—), 2.94 (2H, t, J 7.8, —CH$_2$—), 3.08 [9H, s, $^+$N(CH$_3$)$_3$], 4.53 (2H, s, —CH$_2$N$^+$), 7.23–7.35 (3H, m, 3 of ArH), 7.66 (1H, d, J 7, 1 of ArH) and 13.8 (1H, broad s, NH); m/z (CI$^+$; NH3) 228 [(M—Me)H$^+$; 40%]; m/z (CI$^-$; NH$_3$) 127 (I$^-$; 100%).

n-Butyllithium (2.5 mol dm$^{-3}$; 2.5 cm$^3$) was added cautiously at 0° C. under argon to a stirred suspension of 1-(4-methoxyphenyl)-piperazine dihydrochloride (0.53 g) in THF (10 cm$^3$), giving vigorous effervescence and forming a yellow solution. The solution was added at room temperature to a stirred suspension of (4,5-dihydro-1H-benzo[g]indazol-3-ylmethyl)-trimethylammonim iodide (0.50 g) in THF (15 cm$^3$). The mixture was heated at reflux under argon for 30 minutes, then cooled, poured into water (75 cm$^3$) and extracted with ethyl acetate (50 cm$^3$). The organic phase was dried (MgSO$_4$), filtered and concentrated to give an orange solid which was recrystallised from ethanol to give the title compound (0.21 g; 42%) as white granules, m.p. 207°–208° C. (from EtOH); Found: C, 73.5; H, 6.9; N, 14.7. C$_{23}$H$_{26}$N$_4$O requires C, 73.8; H, 7.0; N, 15.0%. δ$_H$(360 MHz; d$_6$-DMSO) 2.53 [4H, broad s, N(CH$_2$)$_2$], 2.69 (2H, t, J 7.0, —CH$_2$—), 2.87 (2H, t, J 7.0, —CH$_2$—), 3.00 [4H, broad s, N(CH$_2$)$_2$], 3.56 (broad s, —CH$_2$N), 3.67 (3H, s, OCH$_3$), 6.78–6.87 (4H, m$_{AB}$, 4 of ArH), 7.15–7.25 (3H, 3 of ArH), 7.60–7.70 (1H, m, 1 of ArH), 12.57 and 12.96 (1H, 2 x broad s, NH); m/z (CI$^+$; NH$_3$) 375 (MH$^+$; 60%) and 193 (100).

EXAMPLE 2

3-(4-(5-Chloropyridin-2-yl)-piperazin-1-ylmethyl)-4,5-dihydro-1H-benzo[g]indazole A solution of (4,5-dihydro-1H-benzo[g]indazol-3-ylmethyl)-trimethylammonium iodide (0.40 g), 1-(5-chloropyridin-2-yl)-piperazine (0.32 g) and diisopropylethylamine (0.28 cm$^3$) in DMF (10 cm$^3$) was heated under argon at 100° C. for 24 hours. The mixture was cooled, poured into water (25 cm$^3$) and extracted with 10% methanol-dichloromethane (3×15 cm$^3$). The extracts were concentrated and the residual oil was partitioned between water (20 cm$^3$) and 50% ethyl acetate-diethyl ether (20 cm$^3$) to wash away DMF. The organic layer was dried (MgSO$_4$), filtered and concentrated to give a brown solid. Flash column chromatography on silica gel, eluting with 5% methanol-dichloromethane, gave the coupled product as a white solid, which was recystallised from dichloromethane to give the title compound (0.087 g; 21%) as white crystals, m.p. 207°–208° C. (from CH$_2$Cl$_2$); Found: C, 66.3; H, 5.8; N, 18.1. C$_{21}$H$_{22}$N$_5$Cl requires C, 66.4; H, 5.8; N, 18.4%. δ$_H$(360 MHz; d$_6$-DMSO) 2.45–2.50 [4H, m, N(CH$_2$)$_2$], 2.68 (2H, t, J 7.4, —CH$_2$—), 2.84 (2H, t, J 7.4, —CH$_2$—), 3.40–3.48 [4H, m, N(CH$_2$)$_2$], 3.56 (2H, broad s, —CH$_2$N), 6.84 (1H, d, J9.1, 1 of ArH), 7.15–7.24 (3H, m, 3 of ArH), 7.56 (1H, dd; J 9.1 and 2.6, 1 of ArH), 7.60–7.70 (1H, m, 1 of ArH), 8.08 (1H, d, J 2.6, 1 of ArH), 12.56 and 12.98 (1H, 2 x broad s, NH); m/z (CI$^+$; NH$_3$) 380 (MH$^+$; 20%) and 198 (100).

EXAMPLE 3

3-(1,2,3,4-Tetrahydroisoquinolin-2-ylmethyl)-4,5-dihydro-1H-benzo[g]indazole A solution of (4,5-dihydro-1H-benzo[g]indazol-3-ylmethyl)-trimethylammonium iodide (0.40 g), 1,2,3,4-tetrahydroisoquinoline (0.20 cm$^3$) and diisopropylethylamine (0.28 cm$^3$) in DMF (10 cm$^3$) was heated under argon at 80° C. for 24 hours, then stirred at room temperature for 48 hours. The mixture was poured into water (30 cm$^3$) and extracted with ethyl acetate (2×20 cm$^3$). The organic extracts were dried (MgSO$_4$), filtered and concentrated. Flash column chromatography on silica gel, eluting with 5% ethanol-ethyl acetate, gave a yellow oil that crystallised on standing. The material was recrystallised from ethyl acetate-hexane to give the title compound (0.111 g; 33%) as white needles, m.p. 180°–182° C. (from EtOAc-hexane); Found: C, 79.7; H, 6.7; N, 13.1. C$_{21}$H$_{21}$N$_3$ requires C, 80.0; H, 6.7; N, 13.3%. δ$_H$(360 MHz; CDCl$_3$) 2.72–2.80 (4H, m, 2 x —CH$_2$—), 2.90–2.98 (4H, m, 2 x —CH$_2$—), 3.70 (2H, s, —CH$_2$N), 3.73 (2H, s, —CH$_2$N), 6.99 (1H, d, J5.8, 1 of ArH), 7.10–7.28 (6H, m, 6 of ArH) and 7.79 (1H, d, J 7.3, 1 of ArH); m/z (CI$^+$; NH$_3$) 316 (MH$^+$; 100%).

EXAMPLE 4

3-(4-Isoquinolin-3-yl-piperazin-1-ylmethyl)-4,5-dihydro-1H-benzo[g]indazole

A solution of (4,5-dihydro-1H-benzo[g]indazol-3-ylmethyl)-trimethylammonium iodide (0.40 g), 4-isoquinolin-3-yl-piperazine dihydrochloride (0.31 g) and diisopropylethylamine (1.0 cm$^3$) in DMF (5 cm$^3$) was heated under argon at 80° C. for 48 hours. The mixture was cooled, then poured into water (50 cm$^3$) and extracted with 50% diethyl ether-ethyl acetate (2×50 cm$^3$). The organic extracts were dried (MgSO$_4$), filtered and concentrated to give a brown oil that crystallised on standing. The material was recrystallised twice from ethyl acetate-hexane to give the title compound (0.038 g; 9%) as grey granules, m.p. 228°–230° C. (from EtOAc-hexane); Found: C, 75.0; H, 6.3; N, 17.3. C$_{25}$H$_{25}$N$_5$.0.25(H$_2$O) requires C, 75.0; H, 6.4; N, 17.5%. δ$_H$(360 MHz; d$_6$-DMSO) 2.54–2.57 [4H, m, N(CH$_2$)$_2$], 2.71 (2H, t, J 7.0, —CH$_2$—), 2.88 (2H, t, J 7.0, —CH$_2$—), 3.50–3.57 [4H, m, N(CH$_2$)$_2$], 3.59 (2H, broad s, —CH$_2$N), 6.94 (1H, s, 1 of ArH), 7.15–7.28 (4H, m, 4 of ArH), 7.53 (1H, t, J 7.8, 1 of ArH), 7.65 (2H, d, J 8.2, 2 of ArH), 7.85 (1H, d, J 8.1, 1 of ArH), 8.96 (1H, s, 1 of ArH), 12.56 and 12.96 (1H, 2 x broad s, NH); m/z (CI$^+$; NH$_3$) 396 (MH$^+$; 8%), 214 (68), 185 (50), 132 (50), 130 (80), 87 (70) and 61 (100).

EXAMPLE 5

3-(4-Phenyl-1,2,3,6-tetrahydropyridin-1-yl-methyl)-4,5-dihydro-1H-benzo[g]indazole A solution of (4,5-dihydro-1H-benzo[g]indazol-3-ylmethyl)-trimethylammonium iodide (0.41 g), 4-phenyl-1,2,3,6-tetrahydropyridine (0.25 g) and diisopropylethylamine (0.40 cm$^3$) in DMF (15 cm$^3$) was heated under argon at 60° C. for 24 hours. The mixture was cooled, poured into water (50 cm$^3$) and extracted with ethyl acetate (2×25 cm$^3$). The extracts were dried (MgSO$_4$), filtered and concentrated to give brown oil. Flash column chromatography on silica gel, eluting with 5% methanol-dichloromethane+1% ammonia, removed baseline material. Preparative thin layer chromatography on silica, eluting with 2% methanol-dichloromethane+1% ammonia, gave the coupled product as white crystals, which were recrystallised from ethanol to give the title compound (0.045 g; 12%), m.p. 175°–176° C. (from EtOH); Found: C, 80.7; H, 6.7; N, 12.4. C$_{23}$H$_{23}$N$_3$ requires C, 80.9; H, 6.8; N, 12.3%. δ$_H$(360 MHz; CDCl$_3$) 2.68 (2H, broad s, NCH$_2$CH$_2$), 2.76 (2H, t, J 7.7, —CH$_2$—), 2.91–2.99 (4H, m, NCH$_2$CH$_2$ and —CH$_2$—), 3.39 (2H, broad s, NCH$_2$CH=C), 3.87 (2H, broad s, —CH$_2$N), 6.02–6.08 (1H, m, NCH$_2$CH=C), 7.19–7.39 (8H, m, 8 of ArH) and 7.79 (1H, d, J 7.4, 1 of ArH); m/z (CI$^+$; NH$_3$) 342 (MH$^+$; 100%), 185 (90) and 156 (100).

EXAMPLE 6

3-(4-(2-Furan-2-ylethyl)-1,2,3,6-tetrahydropyridin-1-ylmethyl)-4,5-dihydro-1H-benzo[g]indazole A solution of (4,5-dihydro-1H-benzo[g]indazol-3-ylmethyl)-trimethylammonium iodide (0.42 g), 4-(2-furan-2-ylethyl)-1,2,3,6-tetrahydropyridine (0.20 g) and diisopropylethylamine (0.20 cm$^3$) in DMF (10 cm$^3$) was heated under argon at 90° C. for 24 hours. The mixture was cooled, poured into water (50 cm$^3$) and extracted with 10% ethyl acetate-diethyl ether (2×25 cm$^3$). The extracts were dried (MgSO$_4$), filtered and concentrated to give a brown oil. Preparative thin layer chromatography on silica, eluting with 10% methanol-dichloromethane+1% ammonia, gave the title compound as a brown off, which was recrystallised as its half-oxalate salt from ethanol-hexane (0.083 g; 18%), m.p. 205°–208° C. (from EtOH-hexane); Found: C, 70.85; H, 6.5; N, 10.05. C$_{23}$H$_{25}$N$_3$O.0.5(CO$_2$H)$_2$.0.2(H$_2$O) requires C, 70.6; H, 6.5; N, 10.3%. δ$_H$(360 MHz; d$_6$-DMSO) 2.16 (2H, broad s, NCH$_2$CH$_2$), 2.27 (2H, t, J 7.7, —CH$_2$—), 2.67–2.73 (4H, m, 2 × —CH$_2$—), 2.86–2.90 (4H, m, 2 × —CH$_2$—), 3.22 (2H, broad s, NCH$_2$CH=C), 3.88 (2H, broad s, —CH$_2$N), 5.42 (1H, broad s, NCH$_2$CH=C), 6.1 (1H, d, J 3, furyl-H3), 6.33 (1H, dd, J 3 and 2, furyl-H4), 7.18–7.29 (3H, m, 3 of ArH), 7.48 (1H, d, J 2, furyl-H5) and 7.64 (1H, d, J 6.6, 1 of ArH); m/z (CI$^+$; NH$_3$) 360 (MH$^+$; 30%), 204 (50) and 174 (100).

EXAMPLE 7

3-(4-Phenethyl-1,2,3,6-tetrahydropyridin-1-ylmethyl)-4,5-dihydro-1H-benzo[g]indazole A solution of (4,5-dihydro-1H-benzo[g]indazol-3-ylmethyl)-trimethylammonium iodide (0.40 g), 4-phenethyl-1,2,5,6-tetrahydropyridine (0.20 g) and diisopropylethylamine (0.30cm$^3$) in DMF (10 cm$^3$) was heated under argon at 80° C. for 19 hours. The mixture was cooled, poured into water (50 cm$^3$) and extracted with 10% ethyl acetate-diethyl ether (3×25 cm$^3$). The extracts were dried (MgSO$_4$), filtered and concentrated to give a brown oil. Flash column chromatography on silica gel, eluting with 10% methanol-dichloromethane+1% ammonia, gave the coupled product as a red solid, which was recrystallized from ethyl acetate to give the title compound (0.10 g; 25%), m.p. 173°–174° C. (from EtOAc); Found: C, 80.8; H, 7.3; N, 11.3. C$_{25}$H$_{27}$N$_3$.0.125(H$_2$O) requires C, 80.8; H, 7.4; N, 11.3%. δ$_H$(360 MHz; CDCl$_3$) 2.19 (2H, broad s, NCH$_2$CH$_2$), 2.30 (2H, t, J 8.3, —CH$_2$—), 2.68–2.76 (6H, m, 3 × —CH$_2$—), 2.95 (2H, t, J 6.9, —CH$_2$—), 3.09 (2H, broad s, NCH$_2$CH=C), 3.71 (2H, broad s, —H$_2$N), 5.38–5.42 (1H, m, NCH$_2$CH=C), 7.16–7.30 (8H, m, 8 of ArH) and 7.80 (1H, d, J 7.4, 1 of ArH); m/z (CI$^+$; NH$_3$) 370 (MH$^+$; 100%).

EXAMPLE 8

3-(4-Phenylpiperidin-1-ylmethyl)-4,5-dihydro-1H-benzo[g]indazole

A solution of (4,5-dihydro-1H-benzo[g]indazol-3-ylmethyl)-trimethylammonium iodide (0.30 g), 4-phenylpiperidine (0.15 g) and diisopropylethylamine (0.30 cm$^3$) in DMF (10 cm$^3$) was heated under argon at 80° C. for 24 hours. The mixture was cooled, poured into water (25 cm$^3$) and extracted with 50% ethyl acetate-diethyl ether (2×25 cm$^3$). The extracts were dried (MgSO$_4$), filtered and concentrated to give the title compound as a brown oil. This was crystallised as the half-oxalate salt from DMF-ethanol-ethyl acetate (0.045 g; 12%), m.p. 128°–230° C. (from DMF-EtOH-EtOAc); Found: C, 73.85; H, 6.8; N, 10.8. C$_{23}$H$_{25}$N$_3$.0.5(CO$_2$H)$_2$.0.1(H$_2$O) requires C, 73.9; H, 6.8; N, 10.8%. δ$_H$(360 MHz; d$_6$-DMSO; 353K) 1.70–1.92 (4H, m, 2 × NCH$_A$CH$_2$), 2.40–2.56 (2H, m, 2 × NCH$_A$H$_B$CH$_2$; partially obscured by DMSO peak), 2.58–2.64 (1H, m, NCH$_2$CH$_2$CH), 2.78 (2H, t, J 7.5, —CH$_2$—), 2.90 (2H, t, J 7.5, —CH$_2$—), 3.16 (2H, broad d, J 11, 2 × NCH$_A$H$_B$CH$_2$), 3.82 (2H, s, —CH$_2$N), 7.15–7.30 (8H, m, 8 of ArH) and 7.66 (1H, d, J 7.7, 1 of ArH); m/z (CI$^+$; NH$_3$) 344 (MH$^+$; 5%), 235 (5), 185 (18) and 162 (100).

EXAMPLE 9

3-(4-Benzylpiperazin-1-ylmethyl)-4,5-dihydro-1H-benzo[g]indazole

A solution of (4,5-dihydro-1H-benzo[g]indazol-3-ylmethyl)-trimethylammonium iodide (0.50 g), 1-benzylpiperazine (0.20 cm$^3$) and diisopropylethylamine (0.40 cm$^3$) in DMF (10 cm$^3$) was heated under argon at 80° C. for 18 hours. The mixture was cooled, poured into water (50 cm$^3$) and extracted with 10% ethyl acetate-diethyl ether (2×25 cm$^3$). The extracts were dried (MgSO$_4$), filtered and concentrated. Flash column chromatography on silica gel, eluting with 5% methanol-dichloromethane+1% ammonia gave the coupled product as a white solid. This was recystallised from hexane-ethyl acetate to yield the title compound (0.127 g; 33%) as white granules, m.p. 158°–160° C. (from hexane-EtOAc); Found: C, 76.7; 11, 7.2; N, 15.6. C$_{23}$H$_{26}$N$_4$.0.1(H$_2$O) requires C, 76.7; H, 7.3; N, 15.6%. δ$_H$ (360 MHz; d$_6$-DMSO) 2.38 (8H, broad s, 2 × NCH$_2$CH$_2$N), 2.65 (2H, t, J 7.6, —CH$_2$—), 2.84 (2H, t, J 7.6, —CH$_2$—), 3.43 (2H, s, CH$_2$N), 3.49 (2H, broad s, —CH$_2$N), 7.14–7.32 (8H, m, 8 of ArH), 7.65 (1H, broad s, 1 of ArH), 12.51 and 12.96 (1H, 2 × broad s, NH); m/z (CI$^+$; NH$_3$) 359 (MH$^+$; 100%).

EXAMPLE 10

3-(4-Quinolin-2-yl-piperazin-1-ylmethyl)-4,5-dihydro-1H-benzo[g]indazole

A solution of (4,5-dihydro-1H-benzo[g]indazol-3-ylmethyl)-trimethylammonium iodide (0.4 g), 1-(quinolin-2-yl)piperazine (0.23 g) and diisopropylethylamine (0.30 cm$^3$) in DMF (10 cm$^3$) was heated under argon at 80° C. for 48 hours. The mixture was cooled, poured into water (50 cm$^3$) and extracted with 10% ethyl acetate-diethyl ether (2×25 cm$^3$). The extracts were dried (MgSO$_4$), filtered and concentrated. Flash column chromatography on silica gel, eluting with 5% methanol-dichloromethane+1% ammonia, removed baseline material. Preparative thin layer chromatography on silica, eluting with 3% methanol-dichloromethane+1% ammonia, gave the title compound, which was crystallised as the oxalate salt from ethanol to give brown granules (0.026 g; 5%), m.p. 154°–155° C. (from EtOH); Found: C, 64.6; H, 5.5; N, 13.7. C$_{25}$H$_{25}$N$_5$.1.25(CO$_2$H)$_2$.0.15(H$_2$O) requires C, 64.7; H, 5.5; N, 13.7%. δ$_H$(360 MHz; d$_6$-DMSO) 2.73 (2H, t, J 7.7, —CH$_2$—), 2.84 (4H, broad s, 2 × NCH$_2$CH$_2$N), 2.90 (2H, t, J 7.7, —CH$_2$—), 3.79 (4H, broad s, 2 × NCH$_2$CH$_2$N) 7.18–7.30 (5H, m, 5 of ArH), 7.51–7.59 (2H, m, 2 of ArH), 7.65 (1H, d, J 7.6, 1 of ArH), 7.71 (1H, d, J 7.9, 1 of ArH)

and 8.06 (1H, d, J 9.2, 1 of ArH); m/z (CI⁺; NH₃) 396 (MH⁺; 40%) and 214 (100).

EXAMPLE 11

3-(4-((E)-2-Phenylethenyl)-1,2,3,6-tetrahydropyridin-1-ylmethyl)-4,5-dihydro-1H-benzo[g]indazole A solution of (4,5-dihydro-1H-benzo[g]indazol-3-ylmethyl)-trimethylammonium iodide (0.20 g), 4-((E)-2-phenylethenyl)-1,2,3,6-tetrahydropyridine (0.085 g) and diisopropylethylamine (0.10 cm³) in DMF (10 cm³) was heated under nitrogen at 80° C. for 48 hours. The mixture was cooled, poured into water (50 cm³) and extracted with 10% ethyl acetate-diethyl ether (2×50 cm³). The extracts were dried (MgSO₄), filtered and concentrated to give a brown oil. Preparative thin layer chromatography on silica gel, eluting with 5% methanol-dichloromethane+1% ammonia, gave the title compound as a brown foam, which was crystallised as the oxalate salt from ethanol to give beige granules (0.007 g; 3%), m.p. 205°–210° C. (from EtOH); $\delta_H$(360 MHz; d₆-DMSO+CF₃CO₂H) 2.54–2.70 (2H, m, NCH₂CH₂), 2.76 (2H, t, J 7.5, —CH₂—), 2.92 (2H, t, J 7.5, —CH₂—), 3.12–3.32 (1H, m, NCH$_A$H$_B$CH₂), 3.60–3.78 (1H, m, NCH$_A$H$_B$CH₂), 3.82–4.00 (2H, m, NCH₂CH=C), 4.40 (2H, broad s, —CH₂N), 5.90 (1H, s, NCH₂CH=C), 6.60 (1H, d, J 16.3, CH=CHPh), 6.96 (1H, d, J 16.3, CH=CHPh) 7.22–7.35 (6H, m, 6 of ArH), 7.49 (2H, d, J 7.4, 2 of ArH) and 7.64 (1H, d, J 6.6, 1 of ArH); m/z (CI⁺; NH₃) 368 (MH⁺; 10%), 298 (10), 188 (15), 186 (20) and 184 (100). Found: M⁺367.2039. $C_{25}H_{25}N_3$ requires 367.2048.

EXAMPLE 12

3-(4-(4-Methoxyphenyl)-piperazin-1-ylmethyl)-1,4-dihydroindeno[1,2-c]pyrazole A solution of lithium disopropylamide in dry THF (100 cm³) was prepared at room temperature by the addition of n-butyllithium (2.5 mol dm⁻³; 6.5 cm³) to diisopropylamine (2.25 cm³) under argon. The yellow solution was cooled to –78° C. and a solution of 1-indanone (2.12 g) in dry THF (10 cm³) was added dropwise. The yellow solution was stirred at –78° C. for 40 minutes.

Carbonyldiimidazole (1.3 g) was added portionwise to a stirred solution of (4-(4-methoxyphenyl)-piperazin-1-yl)-acetic acid (2.00 g) in 3:1 THF-DMF (40 cm³) at room temperature. After 15 minutes, the solution was cannulated into the above yellow solution. The resulting grey-green slurry was stirred at –78° C. for 15 minutes, then warmed to room temperature and poured into dilute aqueous ammonium chloride (200 cm³). The mixture was extracted with ethyl acetate (100 cm³). The organic extract was dried (MgSO₄), filtered and concentrated to give a brown oil. The oil was redissolved in ethyl acetate (50 cm³) and a saturated solution of hydrogen chloride gas in ethyl acetate (50 cm³) was added. After chilling at 0° C. for 24 hours, the brown precipitate was collected to give 2-(1-hydroxy-2-(4-(4-methoxyphenyl)-piperazin-1-yl)-ethylidene)-indan-1-one dihydrochloride (0.82 g; 23%); $\delta_H$(d₆-DMSO) 3.20–3.70 (8H, m, 2 × NCH₂CH₂N, partly obscured by H₂O signal), 3.62 (2H, s, —CH₂—), 3.71 (3H, s, OCH3), 4.70 (2H, s, —CH₂N), 6.88 (2H, d, J 9, 2 of ArH), 7.03 (2H, d, J 9, 2 of ArH), 7.45 (1H, dd, J 7, 1 of ArH), 7.62–7.59 (2H, m, 2 of ArH) and 8.14 (1H, broad d, J 7, 1 of ArH).

A suspension of 2-(1-hydroxy-2-(4-(4-methoxyphenyl)-piperazin-1-yl)-ethylidene)-indan-1-one dihydrochloride (0.30 g), hydrazine monohydrate (1 cm³) and triethylamine (0.30 cm³) in 1:1 methanol-DMF (10 cm³) was stirred at room temperature under argon for 24 hours. The solution was poured into water (25 cm³) and extracted with ethyl acetate (2×25 cm³). The extracts were dried (MgSO₄), filtered and concentrated. Flash column chromatography on silica gel, eluting with 2% methanol-dichloromethane, gave a yellow solid, which was recrystallised from ethanol-water to give the title compound (0.07 g; 29%) as yellow crystals, m.p. 176°–178° C. (from EtOH-H₂O); $\delta_H$(360 MHz, d₆-DMSO) 2.55–2.58 (4H, m, 2 × NCH₂CH₂N), 3.01–3.04 (4H, m, 2 × NCH₂CH₂N), 3.27 (2H, s, —CH₂—, partly obscured by H₂O signal), 3.58 (2H, s, —CH₂N), 3.67 (3H, s, OCH₃), 6.79 (2H, d, J$_{AB}$ 9.2, 2 of ArH), 6.87 (2H, d, J$_{AB}$ 9.2, 2 of ArH), 7.24 (1H, dd, J 7.4 and 7.4, 1 of ArH), 7.32 (1H, dd, J 7.4 and 7.4, 1 of ArH), 7.51 (1H, d, J 7.4, 1 of ArH), 7.59 (1H, broad d, J 7.4, 1 of ArH) and 12.58 (1H, broad s, NH); m/z (CI⁺; NH₃) 361 (MH⁺; 23%), 214 (30) and 193 (100).

EXAMPLE 13

3-(4-(4-Methoxyphenyl)-piperazin-1-ylmethyl)-benzo-[b]-2H-pyrano[4,8-c]-1H-pyrazole A solution of sodium 1,1,1,3,3,3-hexamethyldisilylazide (1.0 mol dm⁻³; 35 cm³) in THF was added at –78° C. under nitrogen to a stirred solution of 4-chromanone (5.0 g) in dry THF (100 cm³). The bright orange solution was stirred at –78° C. for 20 minutes, followed by addition of diethyl oxalate (4.75 cm³). The mixture was warmed to room temperature, becoming a thick, red gel. The gel was diluted with hydrochloric acid (1.0 mol dm⁻³; 200 cm³) and extracted with ethyl acetate (200 cm³). The extracts were dried (MgSO₄), filtered and concentrated to give hydroxy-(4-oxo-chroman-3-ylidene)-acetic acid ethyl ester (8.3 g; 97%) as a bright yellow, waxy solid; $\delta_H$(250 MHz; d₆-DMSO) 1.30 (3H, t, J 7.5, CO₂CH₂CH₃), 4.30 (2H, q, J 7.5, CO₂CH₂CH₃), 5.18 (2H, s, OCH₂C), 7.04 (1H, d, J 8.5, 1 of ArH), 7.12 (1H, dd, J 8.5 and 8.5, 1 of ArH), 7.58 (1H, dd, J 8.5 and 8.5, 1 of ArH) and 7.79 (1H, d, J8.5, 1 of ArH); m/z (CI⁺; NH₃) 249 (MH⁺; 28%) and 205 (100).

A solution of hydroxy-(4-oxo-chroman-3-ylidene)-acetic acid ethyl ester (5.27 g) and hydrazine monohydrochloride (1.50 g) in ethanol (80 cm³) was heated at reflux under nitrogen for 3 hours. The mixture was cooled, then poured into water (200 cm³) and extracted with ethyl acetate (150 cm³). The extract was dried (MgSO₄), filtered and concentrated to give ethyl benzo-[b]-2H-pyrano-[4,3-c]-1H-pyrazole-3-carboxylate (4.93 g; 95%) as a yellow solid; $\delta_H$(360 MHz; d₆-DMSO) 1.32 (3H, t, J 7.1, CO₂CH₂CH₃), 4.30 (2H, q, J 7.1, CO₂CH₂CH₃), 5.46 (2H, s, OCH₂C), 6.95 (1H, d, J 8, 1 of ArH), 7.02 (1H, dd, J 8, and 8, 1 of ArH), 7.23 (1H, dd, J 8 and 8, 1 of ArH), 7.62 (1H, d, J 8, 1 of ArH) and 14.1 (1H, broad s, NH); m/z (CI⁺; NH₃) 489 (M₂H⁺; 50%) and 245 (MH⁺; 100).

A solution of lithium aluminium hydride in THF (1.0 mol dm⁻³; 3.0 cm³) was added at 0° C. to a stirred solution of ethyl benzo-[b]-2H-pyrano-[3,4-c]-1H-pyrazole-3-carboxylate (0.36 g) in THF (20 cm³) under nitrogen. After 3 hours the reaction was quenched by cautious addition of water (20 cm³), then extracted with ethyl acetate (2×25 cm³). The extracts were dried (MgSO₄), filtered and concentrated to give benzo-[b]-2H-pyrano[4,3-c]pyrazol-3-ylmethanol (0.33 g; 100%) as a yellow solid; $\delta_H$(360 MHz; d₆-DMSO) 4.49 (2H, s, —CH₂OH), 5.29 (2H, s, OCH₂C), 6.89 (1H, d, J 8, 1 of ArH), 6.97 (1H, dd, J 8, and 8, 1 of ArH), 7.17 (1H, dd, J 8 and 8, 1 of ArH), 7.57 (1H, d, J 8, 1 of ArH) and 12.8 (1H, broad s, NH); m/z (CI⁺; NH₃) 218 (MNH₄⁺; 6%) and 203 (MH⁺; 100).

A solution of oxalyl chloride in dichloromethane (2.0 mol dm⁻³; 0.90 cm³) was diluted with dichloromethane (10 cm³) and cooled to 0° C. with stirring. Dimethylformamide (0.14 cm³) was added dropwise, giving vigorous effervescence after a brief induction period. The mixture was stirred at 0° C. for 10 minutes, then warmed to room temperature, forming a white suspension. The suspension was cooled to 0° C. and a solution of (benzo-[b]-2H-pyrano[3,4-c]-1H-pyrazol-3-yl)-methanol (0.33 g) in DMF (2 cm³) was added. The yellow solution was heated at reflux for 2 hours, then cooled and poured into brine (75 cm³). The mixture was extracted with diethyl ether (2×100 cm³). The extracts were dried (MgSO₄), filtered and concentrated to give a yellow oil. The oil was further partitioned between water (30 cm³) and diethyl ether (30 cm³) to wash away residual DMF. The ethereal solution was dried (MgSO₄), filtered and concentrated to give 3-chloromethyl-benzo-[b]-2H-pyrano[4,3-c]-1H-pyrazole (0.285 g; 88%) as a yellow oil; δ_H(250 MHz; d₆-DMSO) 4.78 (2H, s, —CH₂Cl), 5.30 (2H, s, OCH₂O), 6.93–7.05 (2H, m, 2 of ArH), 7.22 (1H, ddd, J 8, 8 and 2, 1 of ArH) and 7.57 (1H, d, J 8, 1 of ArH).

A suspension of 3-chloromethyl-benzo-[b]-2H-pyrano[4,3-c]-1H-pyrazole (0.28 g), 1-(4-methoxyphenyl)piperazine (0.25 g) and potassium carbonate (0.20 g) in DMF (10 cm³) was stirred at room temperature under nitrogen for 48 hours. The mixture was diluted with water (50 cm³) and extracted with 10% ethyl acetate-diethyl ether (2×50 cm³). The extracts were dried (MgSO₄), filtered and concentrated to give a yellow solid, which was recrystallised from ethanol to give the title compound (0.241 g; 58%) as cream-coloured granules, m.p. 190°–192° C. (from EtOH); Found: C, 69.9; H, 6.4; N, 14.5. C₂₂H₂₄N₄O₂.0.1(C₂H₅OH).0.05(H₂O) requires C, 69.8; H, 6.5; N, 14.7%. δ_H(360 MHz; d₆-DMSO) 2.51 (4H, broad s, 2 x NCH₂CH₂N, partly obscured by DMSO signal), 3.01 (4H, broad s, 2 x NCH₂CH₂N), 3.58 (2H, broad s, —CH₂N), 3.67 (3H, s, OCH₃), 5.20–5.36 (2H, m, OCH₂C), 6.79–6.98 (5H, m, 5 of ArH), 6.98 (1H, dd, J 8 and 8, 1 of ArH), 7.17 (1H, dd, J 8 and 8, 1 of ArH), 7.52–7.62 (1H, m, 1 of ArH), 12.84 and 13.14 (1H, 2 x broad s, NH); m/z (CI⁺; NH₃) 377 (MH⁺; 87%) and 193 (100).

Similarly prepared was:

EXAMPLE 14

3-(4-Styryl-3,6-dihydro-2H-pyridin-1-ylmethyl)-1,4-dihydro-5-oxa-1,2-diazacyclopenta[a]naphthalene From 3-chloromethylbenzo[b]-2H-pyrano[4,3-c]-1H-pyrazole and 4-((E)-2-phenylethenyl)-1,2,3,6-tetrahydropyridine.

Pale pink granules, m.p. 177°–179° C. (from EtOAc-Hexane); Found C, 76.75; H,6.7; N, 11.0. C₂₄H₂₅N₃.0.2 (H₂O) requires C, 76.85; H, 6.8; N, 11.2%. δ_H (360 MHz; CDCl₃) 2.04 (2H, broad s, NCH₂CH₂), 2.29 (2H, t, J=8 Hz, CH₂CH₂Ph), 2.62 (2H, t, J=6 Hz, NCH₂CH₂), 2.74 (2H, t, J=8 Hz, CH₂CH₂Ph), 3.02 (2H, broad s, NCH₂CH=C), 3.61 (2H, s, NCH₂Ar), 5.26 (2H, s, OCH₂Ar), 5.39 (1H, broad s, NCH₂CH=C), 6.94–7.02 (2H, m, 2 of ArH), 7.16–7.22 (4H, m, 4 of ArH), 7.26–7.30 (2H, m, 2 of ArH) and 7.71 (1H, dd, J=7.5 Hz and 1.5 Hz, 1 of ArH); m/z (CI⁺; NH₃) 372 (MH⁺; 30%) and 184 (100).

We claim:

1. A compound of formula I, or a pharmaceutically acceptable salt thereof or a prodrug thereof:

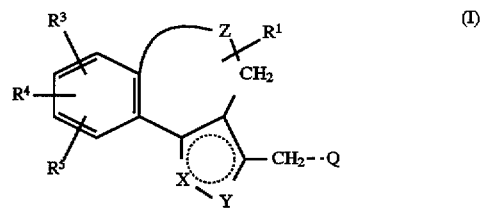

wherein the broken circle represents two non-adjacent double bonds whereby the five-membered ring containing X and Y is aromatic;

one of X and Y represents nitrogen, and the other of X and Y represents N—R²;

Z represents a chemical bond, an oxygen or sulphur atom, or a methylene group;

Q represents a moiety selected from the group consisting of a moiety of formulae Qa, Qb, Qc and Qd:

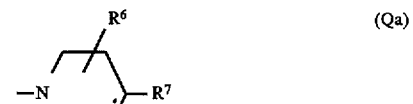

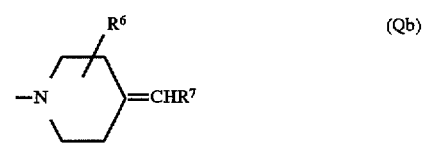

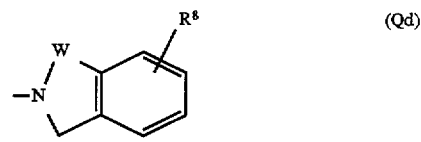

in which the broken line represents an optional chemical bond;

V represents an oxygen atom or a moiety of formula N—R⁷;

R⁶ represents hydrogen, or an optionally substituted C₁₋₆alkyl, C₁₋₆alkoxy, C₂₋₆alkenyl, C₂₋₆alkynyl, C₃₋₇cycloalkyl, C₃₋₇cycloalkyl(C₁₋₆)alkyl, aryl, aryl (C₁₋₆)alkyl, aryl(C₁₋₆)alkoxy, aryl(C₂₋₆)alkenyl, aryl (C₂₋₆)alkynyl, C₃₋₇heterocycloalkyl(C₁₋₆)alkyl, heteroaryl, heteroaryl(C₁₋₆)alkyl, heteroaryl(C₂₋₆) alkenyl or heteroaryl(C₂₋₆)alkynyl group, wherein aryl is selected from phenyl or naphthyl and heteroaryl is selected from the group consisting of pyridyl, quinolyl, isoquinolyl, pyridazinyl, pyrimidinyl, pyrazinyl, pyranyl, furyl, benzofuryl, dibenzofuryl, thienyl, benzthienyl, indolyl, imidazolyl, oxadiazolyl and thiadiazolyl;

R⁷ represents an optionally substituted C₁₋₆alkyl, C₁₋₆alkoxy, C₂₋₆alkenyl, C₂₋₆alkynyl, C₃₋₇cycloalkyl, C₃₋₇cycloalkyl(C₁₋₆)alkyl, aryl, aryl(C₁₋₆)alkyl, aryl (C₁₋₆)alkoxy, aryl(C₂₋₆)alkenyl, aryl(C₂₋₆)alkynyl, C₃₋₇heterocycloalkyl(C₁₋₆)alkyl, heteroaryl, heteroaryl (C₁₋₆)alkyl, heteroaryl(C₂₋₆)alkenyl or heteroaryl (C₂₋₆)alkynyl group, wherein aryl and heteroaryl are defined above;

W represents —CH₂— or —CH₂CH₂—; and

R⁸ represents hydrogen, $C_{1-6}$alkyl, $C_{1-6}$alkoxy, aryl, aryl($C_{1-6}$)alkyl, or halogen;

R¹ and R² independently represent hydrogen or $C_{1-6}$ alkyl;

R³, R⁴ and R⁵ independently represent hydrogen, hydrocarbon, a heterocyclic group, halogen, cyano, trifluoromethyl, nitro, —OR$^a$, —SR$^a$, —SOR$^a$, SO₂R$^a$, —SO₂NR$^a$R$^b$, —NR$^a$R$^b$, —NR$^a$COR$^b$, —NR$^a$CO₂R$^b$, —COR$^a$, —CO₂R$^a$ or —CONR$^a$R$^b$; and R$^a$ and R$^b$ independently represent hydrogen, hydrocarbon or a heterocyclic group.

2. A compound as claimed in claim 1 represented by formula IIA, pharmaceutically acceptable and salts and prodrugs thereof:

(IIA)

wherein

Z is as defined in claim 1;

—T—U represents —CH₂N—, —CH₂CH— or —CH=C—;

A represents —(CH₂)ₙ— or —CH=CH—;

n is zero, 1, 2 or 3;

B represents a group of formula (i), (ii), (iii) or (iv):

(i)  (ii)  (iii)  (iv)

in which E represents oxygen, sulphur or NH; and

R¹³ and R¹⁹ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkoxycarbonyl.

3. A compound as claimed in claim 1 represented by formula IIB, and pharmaceutically acceptable salts and prodrugs thereof:

(IIB)

wherein

Z is as defined in claim 1;

W represents —CH₂— or —CH₂CH₂—;

R¹³ is as defined in claim 2; and

R¹⁸ represents hydrogen, $C_{1-6}$ alkyl, $C_{1-6}$ alkoxy, aryl, aryl($C_{1-6}$)alkyl or halogen.

4. A compound selected from:

3-[4-(4-methoxyphenyl)piperazin-1-ylmethyl]-4,5-dihydro-1H-benzo[g]indazole;

3-[4-(5-chloropyridin-2-yl)piperazin-1-ylmethyl]-4,5-dihydro-1H-benzo[g]indazole;

3-(1,2,3,4-tetrahydroisoquinolin-2-ylmethyl)-4,5-dihydro-1H-benzo[g]indazole;

3-[4-(isoquinolin-3-yl)piperazin-1-ylmethyl]-4,5-dihydro-1H-benzo[g]indazole;

3-(4-phenyl-1,2,3,6-tetrahydropyridin-1-ylmethyl)-4,5-dihydro-1H-benzo[g]indazole;

3-[4-(2-(furan-2-yl)ethyl)-1,2,3,6-tetrahydropyridin-1-ylmethyl]-4,5-dihydro-1H-benzo[g]indazole;

3-[4-(2-phenylethyl)-1, 2,3,6-tetrahydropyridin-1-ylmethyl]-4,5-dihydro-1H-benzo[g]indazole;

3-(4-phenylpiperidin-1-ylmethyl)-4,5-dihydro-1H-benzo[g]indazole;

3-(4-benzylpiperazin-1-ylmethyl)-4,5-dihydro-1H-benzo[g]indazole;

3-[4-(quinolin-2-yl)piperazin-1-ylmethyl]-4,5-dihydro-1H-benzo[g]indazole;

3-[4-((E)-2-phenylethenyl)-1,2,3,6-tetrahydropyridin-1-ylmethyl]-4,5-dihydro-1H-benzo[g]indazole;

3-[4-(4-methoxyphenyl)piperazin-1-ylmethyl]-1,4-dihydroindeno[1,2-c]pyrazole;

3-[4-(4-methoxyphenyl)piperazin-1-ylmethyl]benzo[b]-2H-pyrano[4,3-c]-1H-pyrazole;

pharmaceutically acceptable and salts and prodrugs thereof.

5. A pharmaceutical composition comprising a compound as claimed in claim 1 in association with a pharmaceutically acceptable carrier.

6. A method for the treatment and/or prevention of disorders of the dopamine system, which method comprises administering to a patient in need of such treatment an effective amount of a compound as claimed claim 1.

* * * * *